US 010874414B2

(12) United States Patent
Pepper et al.

(10) Patent No.: US 10,874,414 B2
(45) Date of Patent: Dec. 29, 2020

(54) TISSUE RELEASE INSTRUMENT AND METHODS OF USE

(71) Applicant: Nextremity Solutions, Inc., Warsaw, IN (US)

(72) Inventors: John R Pepper, Cheshire, CT (US); John Early, Dallas, TX (US); Ryan Schlotterback, Fort Wayne, IN (US); Michael Coon, Warsaw, IN (US)

(73) Assignee: NEXTREMITY SOLUTIONS, INC., Warsaw, IN (US)

(*) Notice: Subject to any disclaimer, the term of this patent is extended or adjusted under 35 U.S.C. 154(b) by 148 days.

(21) Appl. No.: 16/107,726

(22) Filed: Aug. 21, 2018

(65) Prior Publication Data

US 2019/0216488 A1     Jul. 18, 2019

Related U.S. Application Data

(60) Provisional application No. 62/535,483, filed on Jul. 21, 2017.

(51) Int. Cl.
*A61B 17/32*   (2006.01)
*A61B 17/02*   (2006.01)

(52) U.S. Cl.
CPC .... *A61B 17/320016* (2013.01); *A61B 17/025* (2013.01); *A61B 17/320036* (2013.01); *A61B 2017/320052* (2013.01)

(58) Field of Classification Search
CPC .......... A61B 17/320016; A61B 17/025; A61B 17/320036; A61B 17/320052
See application file for complete search history.

(56) References Cited

U.S. PATENT DOCUMENTS

| | | | |
|---|---|---|---|
| 5,569,283 A * | 10/1996 | Green | A61B 17/320036 30/162 |
| 5,968,061 A | 10/1999 | Mirza | |
| 7,041,115 B2 | 5/2006 | Mirza et al. | |
| 7,625,374 B2 * | 12/2009 | Branch | A61B 17/1671 606/84 |
| 8,425,509 B2 * | 4/2013 | Longo | A61B 17/320016 606/45 |
| 8,834,508 B2 * | 9/2014 | Chin | A61B 17/025 606/191 |
| 8,911,470 B2 | 12/2014 | Mirza et al. | |
| 8,979,880 B2 | 3/2015 | Mirza et al. | |
| 9,066,746 B2 | 6/2015 | Mirza et al. | |
| 9,179,930 B2 | 11/2015 | Mirza et al. | |
| 9,211,136 B1 | 12/2015 | Mirza et al. | |
| 9,408,623 B2 | 8/2016 | Mirza et al. | |
| 9,445,830 B2 | 9/2016 | Mirza et al. | |
| 9,808,274 B2 * | 11/2017 | Mirza | A61B 1/00087 |
| 2006/0030856 A1 * | 2/2006 | Drewry | A61B 17/025 606/90 |
| 2014/0066963 A1 | 3/2014 | Mirza et al. | |
| 2014/0066964 A1 * | 3/2014 | Mirza | A61B 17/320036 606/170 |

(Continued)

*Primary Examiner* — Julian W Woo
(74) *Attorney, Agent, or Firm* — Heslin Rothenberg Farley & Mesiti P.C.; Victor A. Cardona, Esq.

(57) ABSTRACT

A device for releasing soft tissue includes a distractor and blade assembly. The distractor may include a guide channel positioned along an edge of the distractor and the blade assembly fits into the guide channel and is configured to slide within the channel of the distractor.

12 Claims, 14 Drawing Sheets

(56) References Cited

U.S. PATENT DOCUMENTS

2016/0317177 A1 11/2016 Mirza et al.
2016/0353973 A1 12/2016 Mirza et al.
2016/0354103 A1 12/2016 Mirza et al.

* cited by examiner

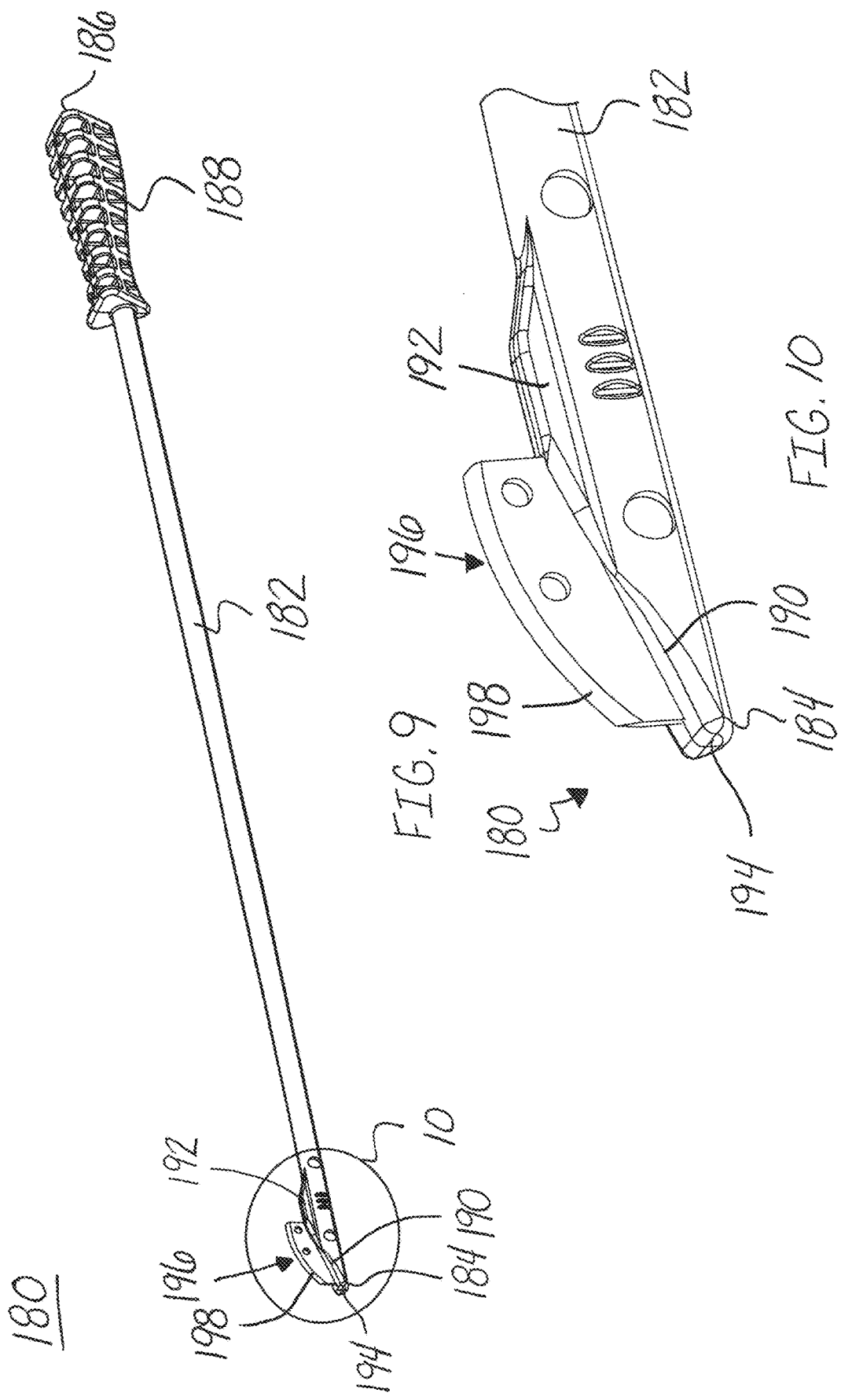

TISSUE RELEASE INSTRUMENT AND METHODS OF USE

CROSS-REFERENCE TO RELATED APPLICATION

This application claims priority to U.S. Provisional Application No. 62/535,483 filed on Jul. 21, 2018, the entire disclosure of which is incorporated by reference.

FIELD OF THE INVENTION

The present invention relates to general surgery, and more particularly orthopedic surgery. More specifically, but not exclusively, the present invention concerns instruments, devices and methods used during surgery for releasing soft tissue.

BACKGROUND

Soft tissue imbalance is one of the primary causes for joint pain and dysfunction. One such example is the contracture of the gastrocnemius muscle, resulting in inadequate range of motion for the ankle. Such limited range of motion can result in increased stresses placed throughout the foot and ankle creating a cascade of bone, joint, and soft tissue issues. It has been found that where conservative treatment fails, a surgical lengthening of the source soft tissues can relieve the imbalance. Muscle tissue is encased in tendinous fascia tissue. When this fascia is cut perpendicular to the direction of muscle tension, it allows the entire muscle complex to lengthen, allowing a return to full joint mobility. Thus, new and improved instruments, assemblies, and methods for isolating the target contracted tissue and cutting (resecting) the tissue to achieve lengthening of the target tissue.

SUMMARY

In one aspect, provided herein is a tissue release instrument. The instrument may include, for example, a distractor and a blade assembly. The distractor including a guide channel positioned along an edge of the distractor, in which the blade assembly engages the guide channel and is configured to slide within the channel of the distractor.

In another aspect, provided herein is a surgical method for using an instrument to release soft tissue. The method may include, for example, making an incision and dissecting between two tissue structures. The method may also include obtaining the instrument with a distractor and a blade assembly and inserting the distractor between the two tissue structures. The method may further include rotating the distractor to expand the space between the two tissue structures and engaging the blade assembly with the distractor. In addition, the method may include moving the blade assembly through the channel of the distractor to make a cut. Finally, the method may include rotating the instrument and returning the distractor to an insertion position and removing the instrument from the incision.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

FIG. 9 is a side perspective view of the blade assembly of the release instrument of FIG. 1, in accordance with an aspect of the present invention;

FIG. 10 is an enlarged view of the first end of the blade assembly of the release instrument of FIG. 9, in accordance with an aspect of the present invention;

DETAILED DESCRIPTION

Generally stated, disclosed herein are embodiments of instruments and devices for releasing soft tissue. Further, methods used during surgery for releasing soft tissue are also disclosed.

In this detailed description and the following claims, the words proximal, distal, anterior, posterior, medial, lateral, superior, and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Figure 16:
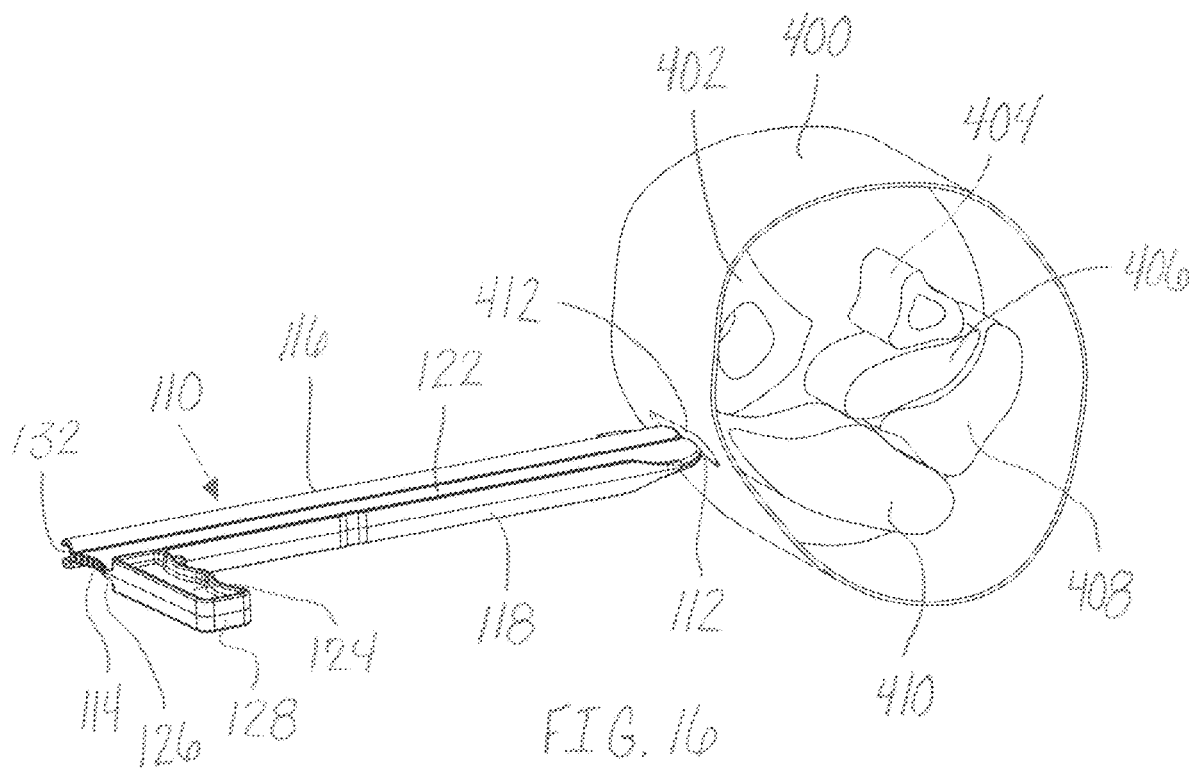
FIG. 16 is a top perspective view of the distractor of the release instrument of FIG. 1 and a cross-section of a portion of a lower leg, in accordance with an aspect of the present invention.
Figure 17:
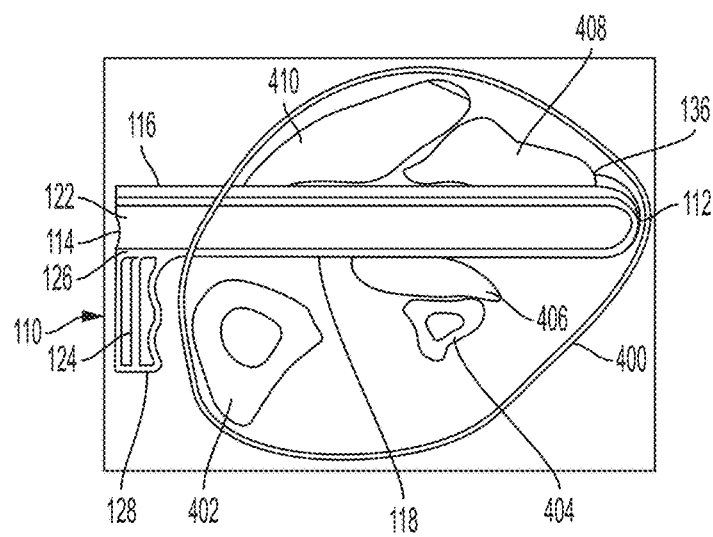
FIG. 17 is a top view of the cross-section portion of the leg of FIG. 16 and a side view of the distractor of the release instrument of FIG. 1 inserted into the leg and rotated, in accordance with an aspect of the present invention.

Referring to the drawings, wherein like reference numerals are used to indicate like or analogous components throughout the several views, and with particular reference to FIGS. 1-17, there is illustrated a release instrument 100. The release instrument 100 includes a guide member, distractor or muscle distractor 110, a protection member or protector 140, and a blade assembly 180. The release instrument 100 may be used, for example, for cutting a patient's soft tissue or other anatomical features. For example, the release instrument 100 may be used to relieve contracted soft tissue or tissue imbalance that is causing joint pain and dysfunction. Specifically, the release instrument 100 may be used, for example, to relieve contracture of the gastrocnemius muscle 408, 410, as shown in FIGS. 16 and 17. Contracture of the gastrocnemius muscle 408, 410 can result in inadequate range of motion for the ankle, which may cause increased stresses to be placed throughout the foot and ankle and thus, creating a cascade of bone, joint and soft tissue issues. To relieve and correct the soft tissue imbalance when conservative treatments fail, a surgical lengthening procedure targeting the source soft tissues may be performed. The release instrument 100 may be used, for example, to perform the lengthening procedure.

Figure 5:
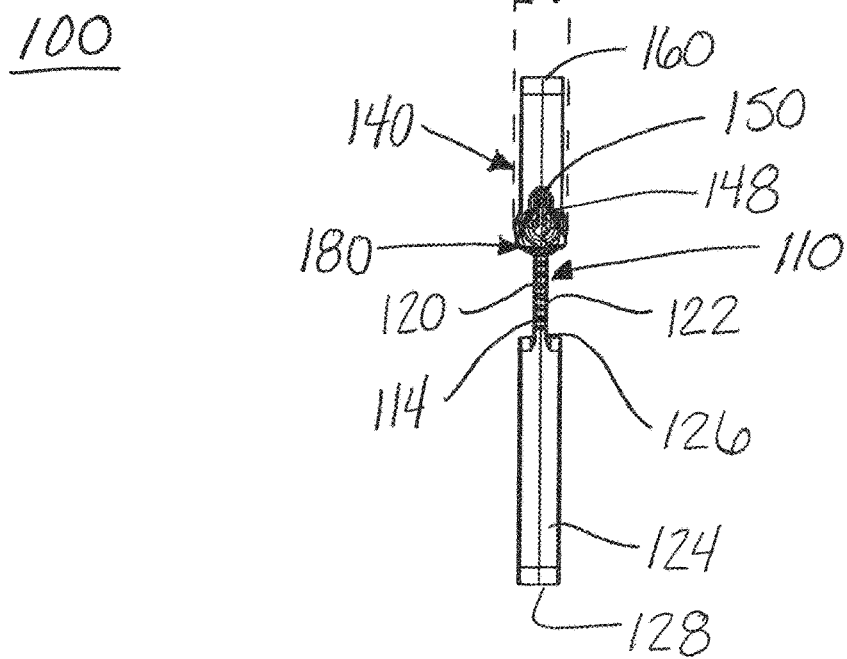
FIG. 5 is a second end view of the release instrument of FIG. 1, in accordance with an aspect of the present invention.
Figure 6:
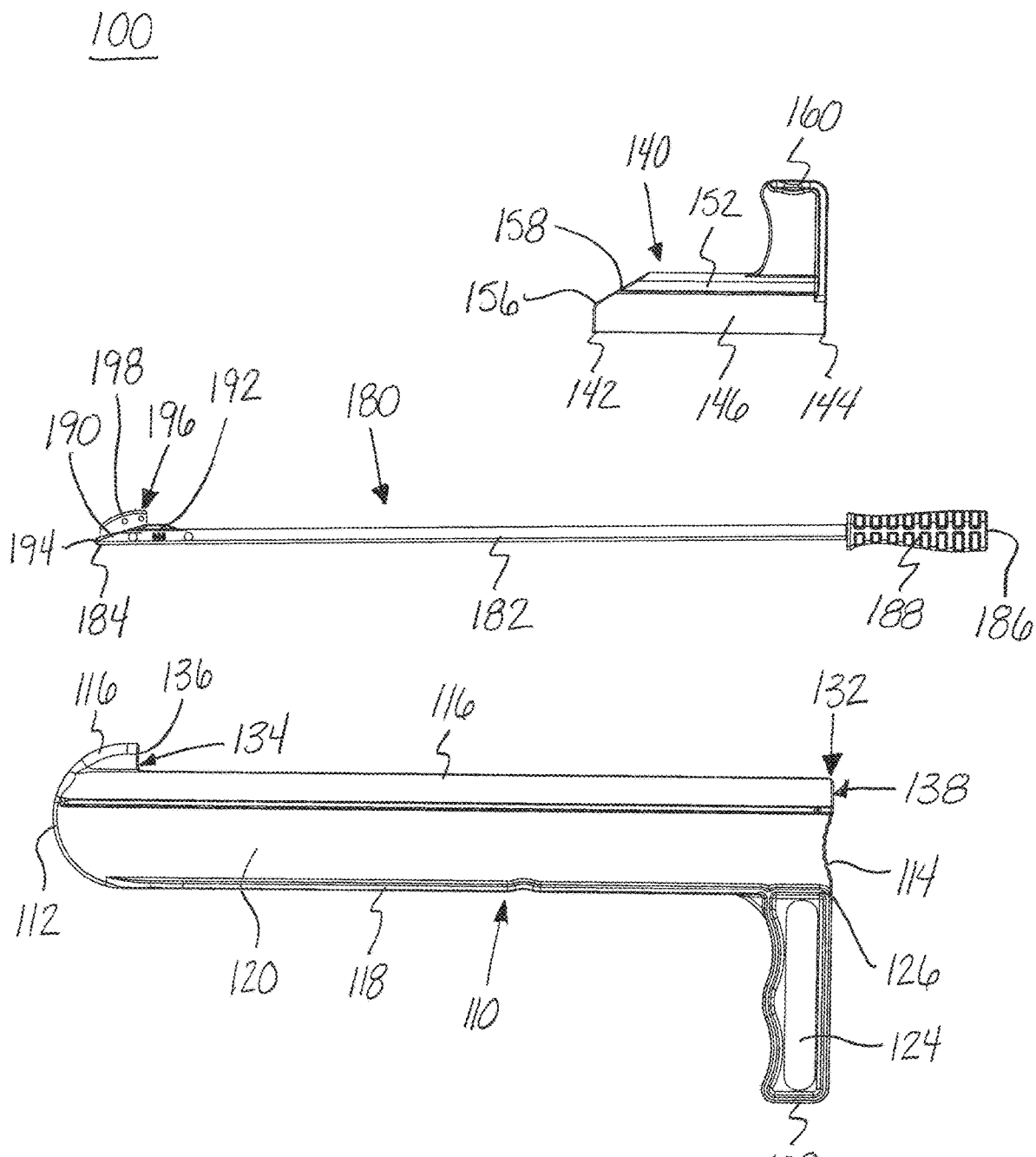
FIG. 6 is an exploded, side view of the release instrument of FIG. 1, in accordance with an aspect of the present invention.
Figure 7:
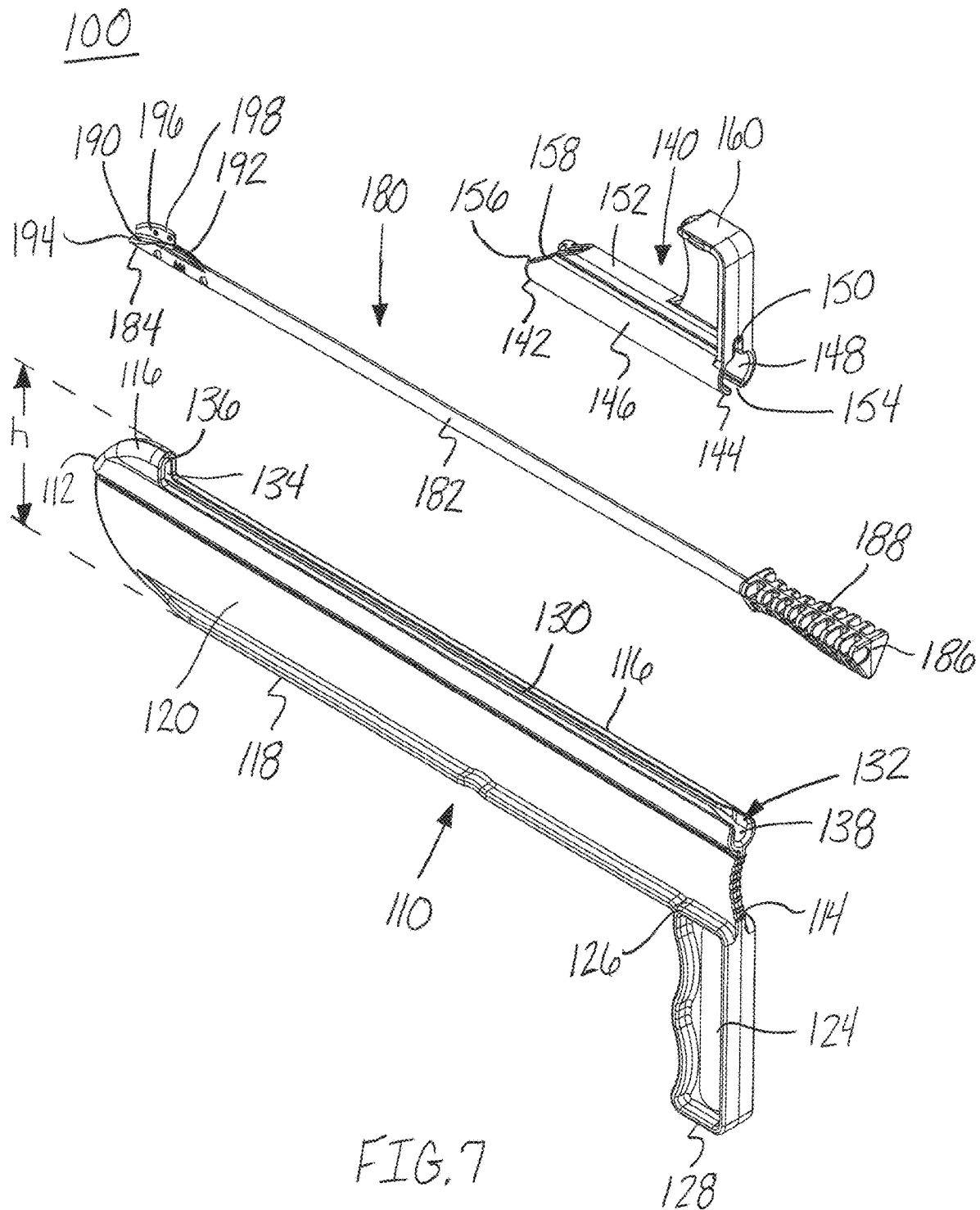
FIG. 7 is an exploded, top perspective view of the release instrument of FIG. 1, in accordance with an aspect of the present invention.

As shown in FIGS. 1-4, 6-8 and 11-15, the guide member, distractor, or muscle distractor 110 may have a first end, blunt end, or bulbous end 112 opposite a second end 114, a top surface 116 opposite a bottom surface 118, and a first side 120 opposite a second side 122. The guide member 110 may have a height "h" extending between the top surface 116 and bottom surface 118 of the first end 112, as shown in FIG. 7. The height "h" may range from, for example, approximately 4 mm to 75 mm and more preferably approximately 20 mm to 25 mm. The height "h" may correspond to, for example, the desired amount of separation between the muscles or tissue structures during cutting. The guide member may also have a width extending between the first side 120 and the second side 122. The width "w" may range from, for example, approximately 0.5 mm to 15 mm and more preferably approximately 1 mm to 3 mm. For example, the top surface 116 surrounding the guide channel 130 and hole 138 may have a width "w" extending between the first side 120 and the second side 122, as shown in FIG. 5. The guide member 110 may have a height "h" to width "w" ratio of, for example, approximately 1:1 to 20:1 and, more preferably, a ratio around 5:1.

Figure 1:
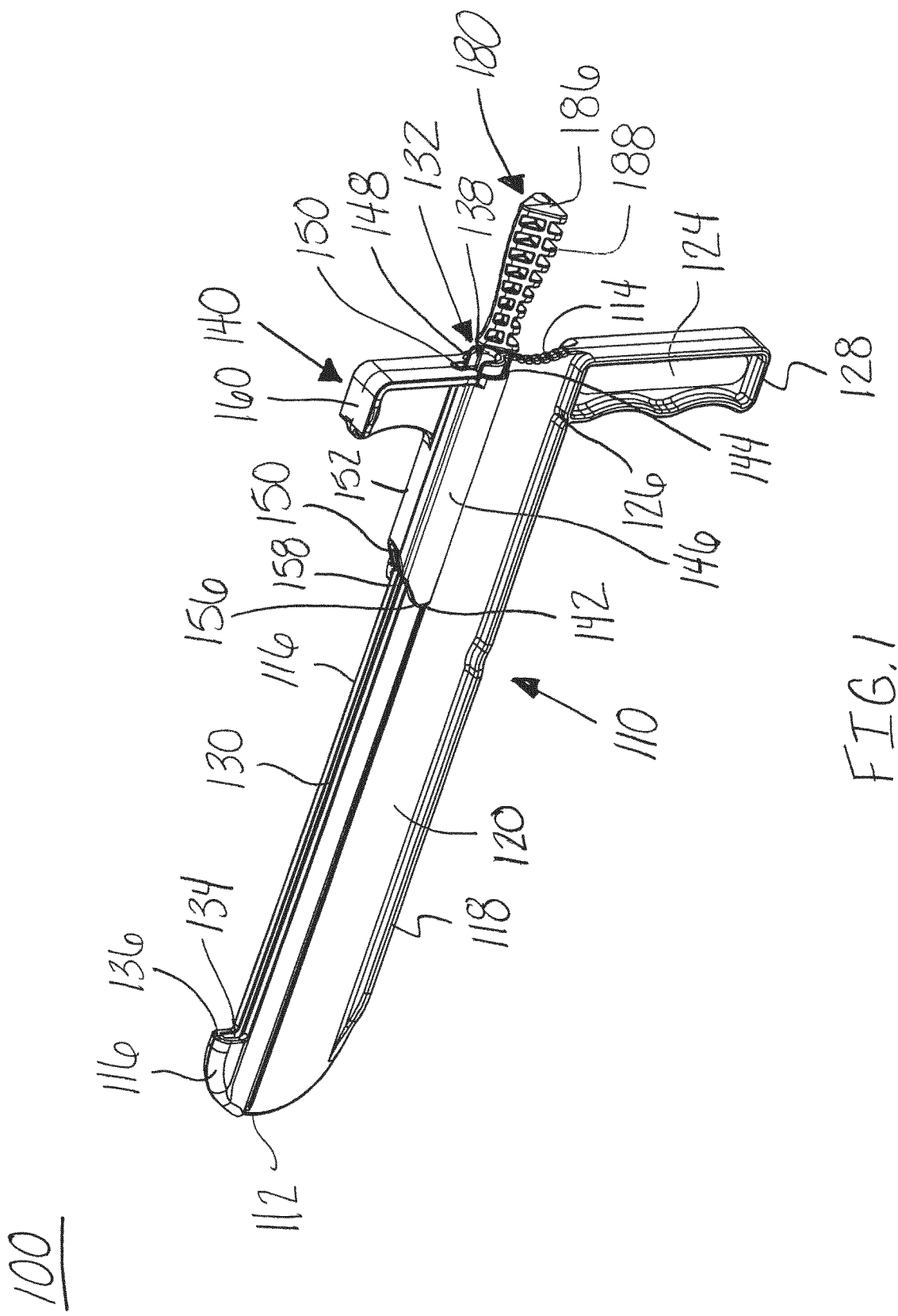
FIG. 1 is a top perspective view of a release instrument, in accordance with an aspect of the present invention.
Figure 2:
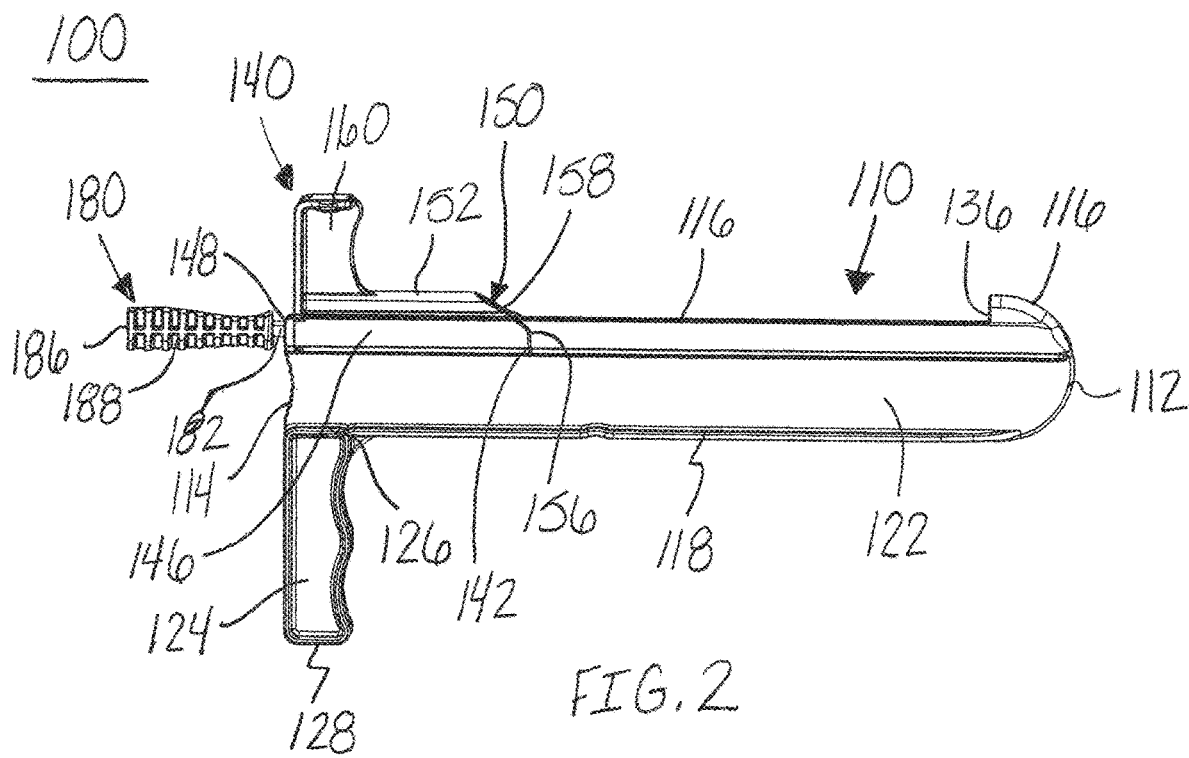
FIG. 2 is a side view of the release instrument of FIG. 1, in accordance with an aspect of the present invention.
Figure 3:
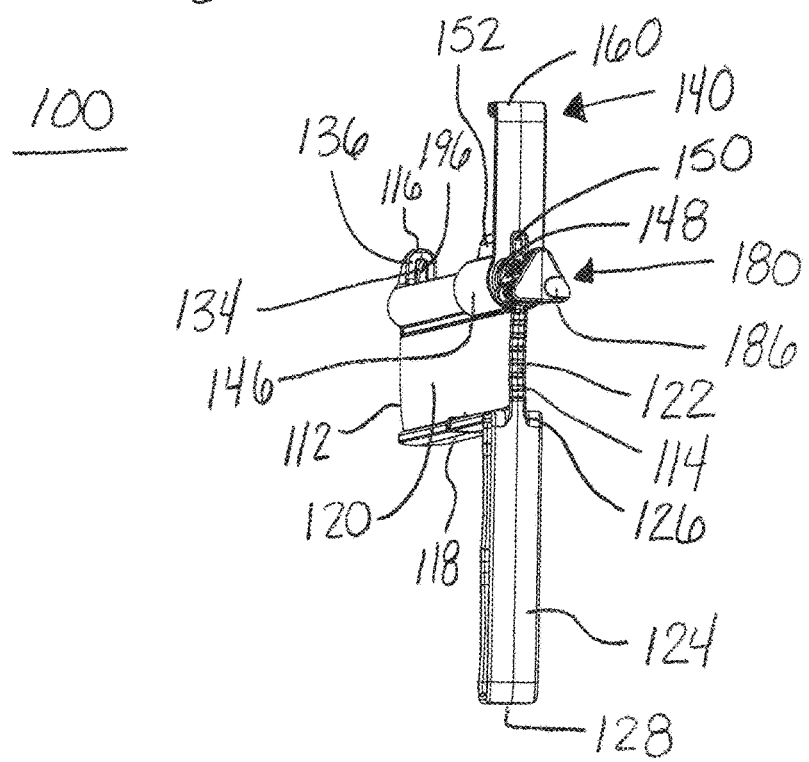
FIG. 3 is a second end perspective view of the release instrument of FIG. 1, in accordance with an aspect of the present invention.
Figure 4:
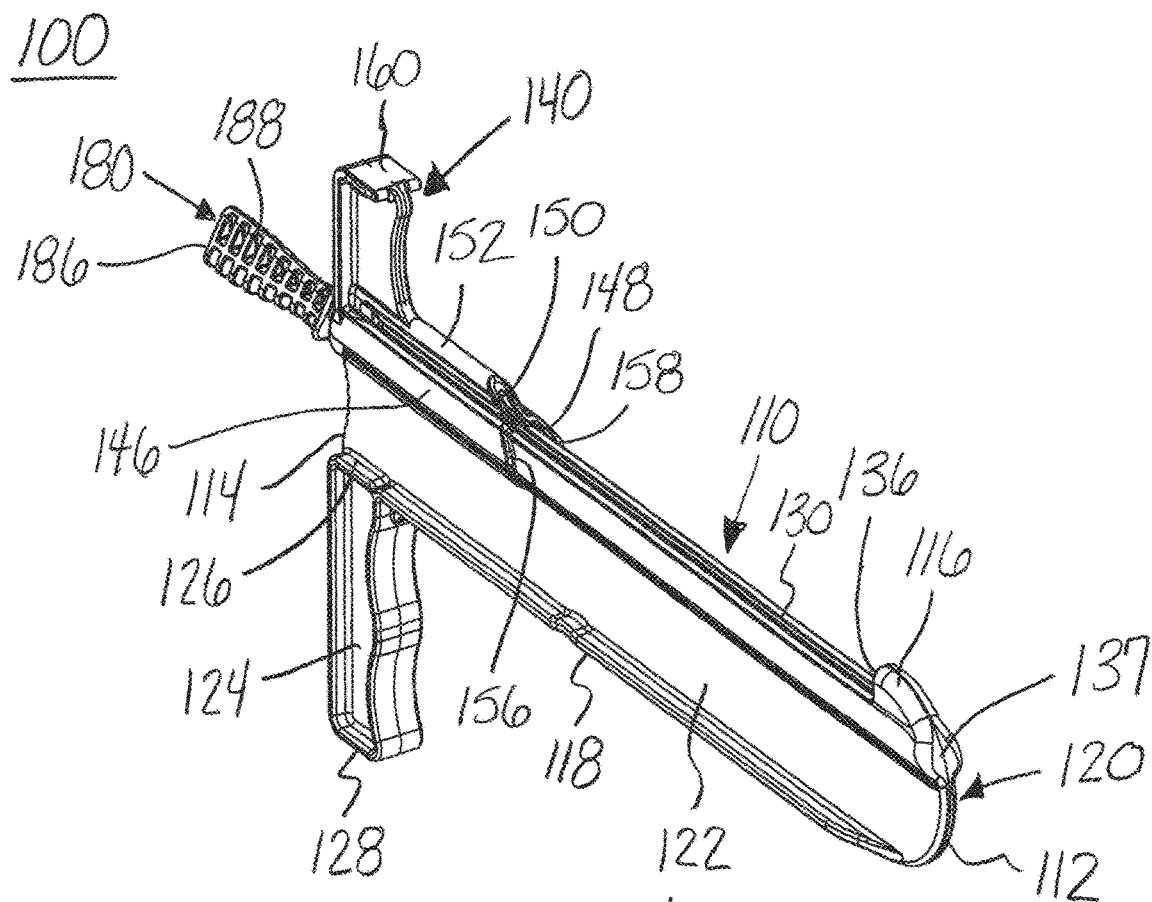
FIG. 4 is a first end perspective view of the release instrument of FIG. 1, in accordance with an aspect of the present invention.

With continued reference to FIGS. 1-4, 6-8 and 11-15, the first end 112 may be, for example, curved from the top surface 116 to the bottom surface 118 forming a semi-circle or similar blunt profile. The first end 112 may also include a nose portion 137, as shown in FIG. 4. The nose portion 137 may be, for example, wider than the top surface 116 and wider than the width between the first and second sides 120, 122. In addition, the top surface 116 may have two varying height portions, for example, a first portion at the first end 112 and a second recessed portion extending from a hook portion 136 to the second end 114. The second recessed portion of the top 116 may have, for example, a generally circular or round exterior surface. The exterior surface of the second recessed portion of the top 116 may extends to the first end 112 below the hook portion 136. The sides 120, 122 include, for example, at least a portion between the top surface 116 and the bottom surface 118 that is flat.

The guide member 110 may also include a handle 124 positioned near the second end 114 and extending away from the bottom surface 118, as shown in FIGS. 1-8 and 11-15. The handle 124 may have a first end 126 and a second end 128. The first end 126 may be coupled to the bottom surface 118 of the guide member 110. The handle 124 may be, for example, aligned with the second end 114 of the guide member 110 and positioned generally perpendicular to the longitudinal axis of the guide member 110. The handle 124 may be configured or sized and shaped to be grasped by a hand of, for example, a surgeon or other medical professional for inserting, activating and removing the guide member 110 from a patient. For example, the handle 124 may assist with insertion of the guide member 110 into a patient and rotation of the distractor 110 ninety degrees (90°) to separate the gastrocnemius muscle 408, 410 from the soleus muscle 406, as shown in FIG. 17.

Referring now to FIGS. 7, 11, 13 and 15, the guide member 110 may also include a channel or guide element 130 extending from the second end 114 to a position near the first end 112, along the top side 116 of the guide member 110. The channel 130 may extend into the guide member 110 from the recessed portion of the top surface 116 and engage a hole or opening 138 extending from the second end 114 to a position near the first end 112. The hole 138 may have, for example, a generally circular cross-section to correspond to the shape of the exterior of the blade assembly 180. The width of the channel 130 may be, for example, smaller than the diameter of the hole 138. The second end 114 may also have a blade insertion end or an open end 132 providing an access point on the second end 114 of the guide member 110 to the channel 130 and the hole 138 for inserting the blade assembly 180. The open end 132 provides access to the hole 138 at the second end 114 for receiving the shaft 182 of the blade assembly 180. The shaft 182 may be aligned with the hole 138 and the blade member 196 may be aligned with the channel 130 during insertion of the blade assembly 180 into the guide member 110. The first end 112 of the guide member 110 may also include a blade receiving member or cavity 134. The cavity 134 may receive and cover the blade member 196 of the blade assembly 180, for example, to prevent the blade member 196 from cutting any tissues or organs during removal of the release instrument 100 from a patient. In addition, the guide member 110 may include a lip or hook portion 136 near the first end 112. The hook portion 136 may be positioned adjacent to the cavity 134 and may extend above the channel 130. The lip or hook portion 136 may be sized and shaped or configured, for example, to engage the lateral muscle belly of the gastrocnemius 408, as shown in FIG. 17, and assist with the stabilization of the release instrument 100 during the cutting of the soft tissue. The hook portion 136 provides, for example, an anchor point for the distractor 110 and provides a counter force for the user as force is exerted to cut the tissue structures. Further, the hook portion 136 may act as, for example, a blunt dissection tool to assist with the dissection or cutting of the tissue structures.

The protection member, protector, or shield 140 may include a first end 142 and a second end 144, as shown in FIGS. 1, 2, 4, 6-8, and 11-15. The shield 140 may include an engagement member 146 and a handle portion or handle 160. The handle 160 may extend away from a top of the engagement member 146 in a generally perpendicular orientation. The handle 160 may allow for the shield 140 to be translated along the top 116 of the guide member 110 around the exterior surface of the channel 130 to move tissue from the path of the shield 140 and blade assembly 180.

Figure 8:
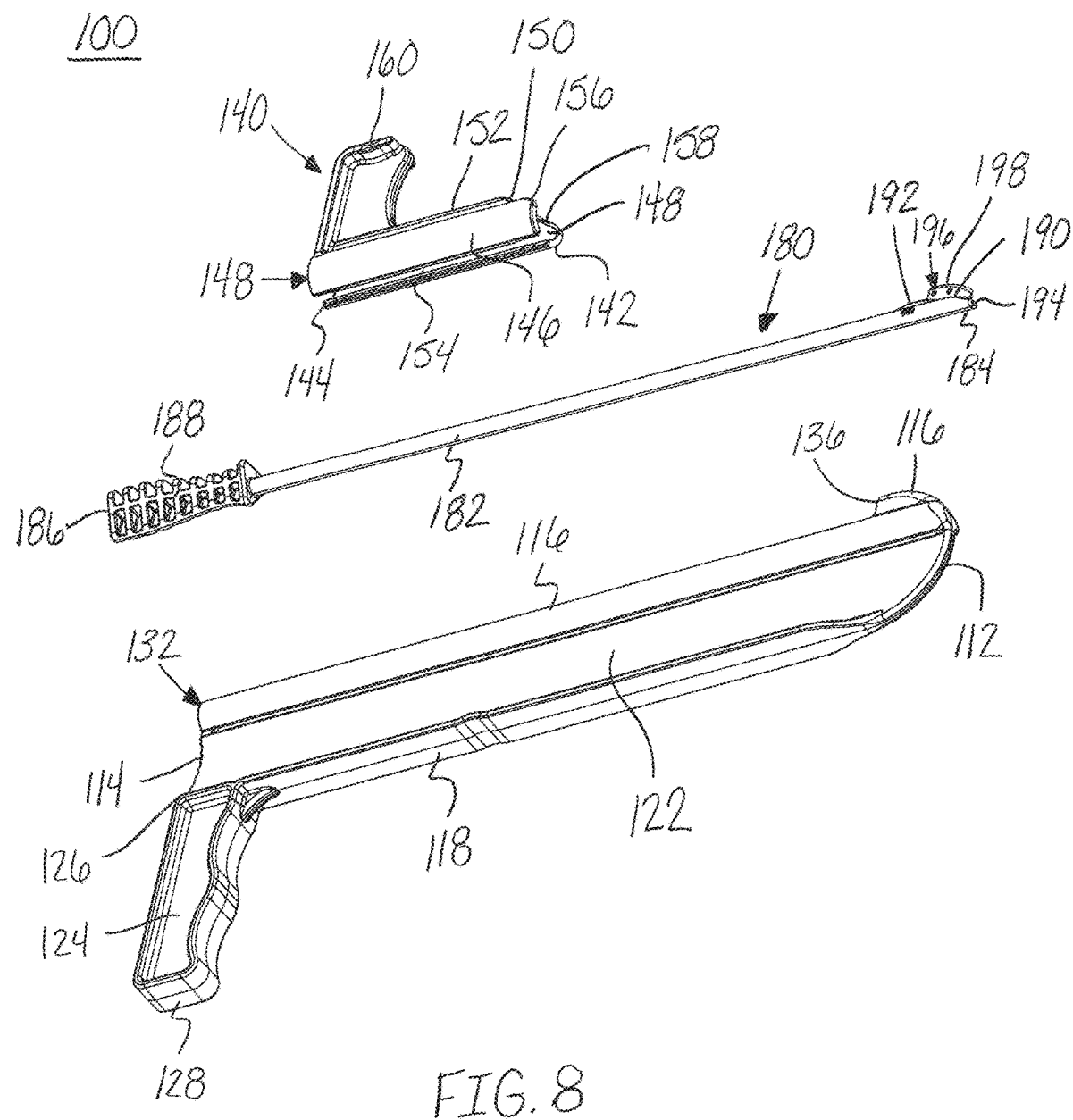
FIG. 8 is an exploded, bottom perspective view of the release instrument of FIG. 1, in accordance with an aspect of the present invention.

With continued reference to FIGS. 7 and 8, the shield 140 may also include a through hole 148 extending through the shield from the first end 142 to the second end 144. The through hole 148 may be, for example, sized and shaped or configured to slide onto the top 116 of the guide member 110. The through hole 148 may, for example, have a generally round cross section, as shown in FIG. 7. The shield 140 may also include a passageway or blade channel 150 extending from the through hole 148 toward a top of the outer surface 152 of the shield 140. The blade channel 150 may extend from the first end 142 to the second end 144 and be sized and shaped or configured to receive a blade member 196 of the blade assembly 180. In addition, the shield 140 may include an engagement channel 154 forming an opening or passageway into the through hole 148 from a bottom surface of the engagement member 146. The engagement channel 154 may extend from the first end 142 to the second end 144 and be sized and shaped or configured to receive the guide member 110. Specifically, the sides 120, 122 of the guide member 110 may be aligned and received within the engagement channel 154. For example, the interior surface of the through hole 148 may surround the exterior surface or top portion 116 of the guide member 110 surrounding the channel 130 and hole 138. The passageway 150 may be positioned on an exterior of the through hole 148 generally opposite or aligned with the engagement channel 154. The shield 140 may also include a leading edge 156 at the first end 142. The leading edge 156 may be shaped to push or move tissue from the path of the shield 140 as it translates along the guide member 110. A portion of the leading edge 156 may be, for example, angled between a top and bottom surface of the shield 140 and the top of the shield 140 forming a tapered or angled portion 158.

Referring now to FIGS. 6-10, the blade assembly 180 is shown. The blade assembly 180 may include a first end 184 and a second end 186. The blade assembly 180 may also include, for example, an elongated shaft or rod 182, a handle 188 at the second end 186, and a blade member or cutting blade 196 at the first end 184. The elongated shaft 182 may include a nose portion or tapered surface 190 and a protrusion or extension member 192 at the first end 184 of the blade assembly 180. The nose portion 190 and protrusion 192 form a tapered surface for receiving and coupling to a blade member 196. The nose portion 190 may also include a blunt tip 194 at the first end 184 or base of the nose portion 190.

The blade member 196 may also include a cutting surface or edge 198 for cutting a patient's tissue, as shown in FIGS. 6-10. The cutting surface or blade edge 198 may have, for example, an arced or curved shape, as shown in FIGS. 6, 9 and 10. In addition, the trailing edge of the blade member 196 or portion of the blade member 196 positioned at least partially within the protrusion 192 may also have a sharp edge for cutting tissue, when needed. The maximum height of the blade member 196 may be, for example, achieved proximal to the leading edge of the cutting surface 198. The maximum height of the blade member 196 may be, for example, the length of the blade, where the height is measured in a direction perpendicular to the elongated shaft and the length is measured in the direction extending parallel to the elongated shaft 182. The maximum height of the blade member 196 may determine, for example, the depth of the cut made to the tissue or fascia. In an embodiment, the blade assembly 180 may include a blade height adjustment member (not shown) positioned proximate to the blade member 196. The blade height adjustment member (not shown) may be, for example, translated or rotated with respect to the blade member 196 to adjust the height of the blade member 196 that protrudes above the top surface 116 of the guide channel 130. The blade height adjustment member (not shown) may be configured to translate with the blade assembly 180 as it translates along the length of the guide member 110.

As shown in FIGS. 11-15, a method of using and assembling the release instrument 100 is shown. The release instrument 100 may be assembled by sliding the first end 142 of the protector 140 onto the second end 114 of the guide member 110 allowing for the protector 140 to translate along the top 116 of the guide member 110. Next, the first end 184 of the blade assembly 180 may be inserted into the second end 114 of the guide member 110. Specifically, the blade assembly 180 may be aligned and inserted into the guide channel 130 and hole 138 of the guide member 110. The blade assembly 180 is configured or sized and shaped to slide within the guide channel 130 and hole 138 of the distractor 110 to cut the fascia of muscles or tissue structures positioned adjacent to the top 116 of the distractor 110. The blade member 196 of the blade assembly 180 may also be configured or sized and shaped to pass through the passageway 150 in the protector 140.

Figure 11:
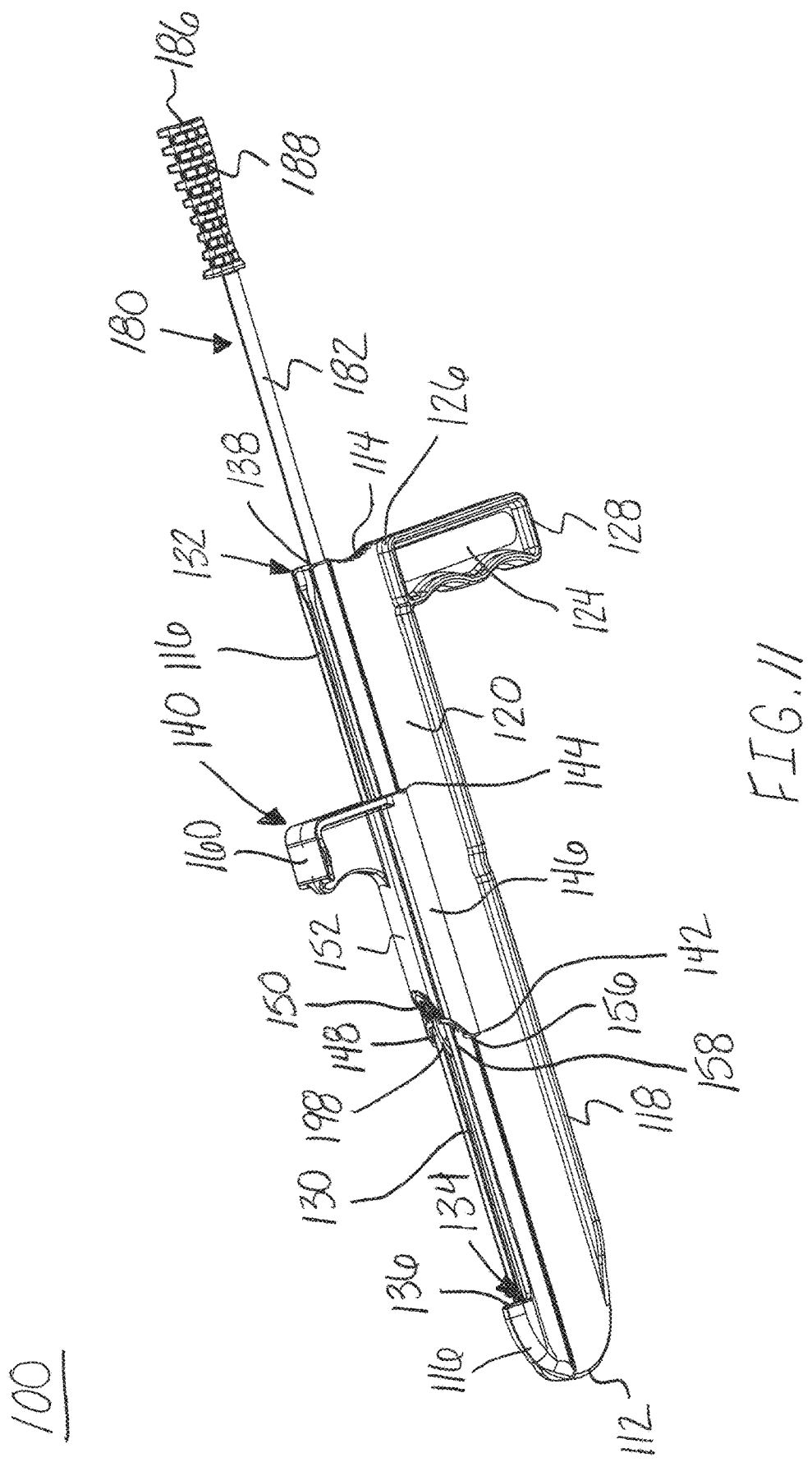
FIG. 11 is a perspective view of the release instrument of FIG. 1 in a first position, in accordance with an aspect of the present invention.
Figure 12:
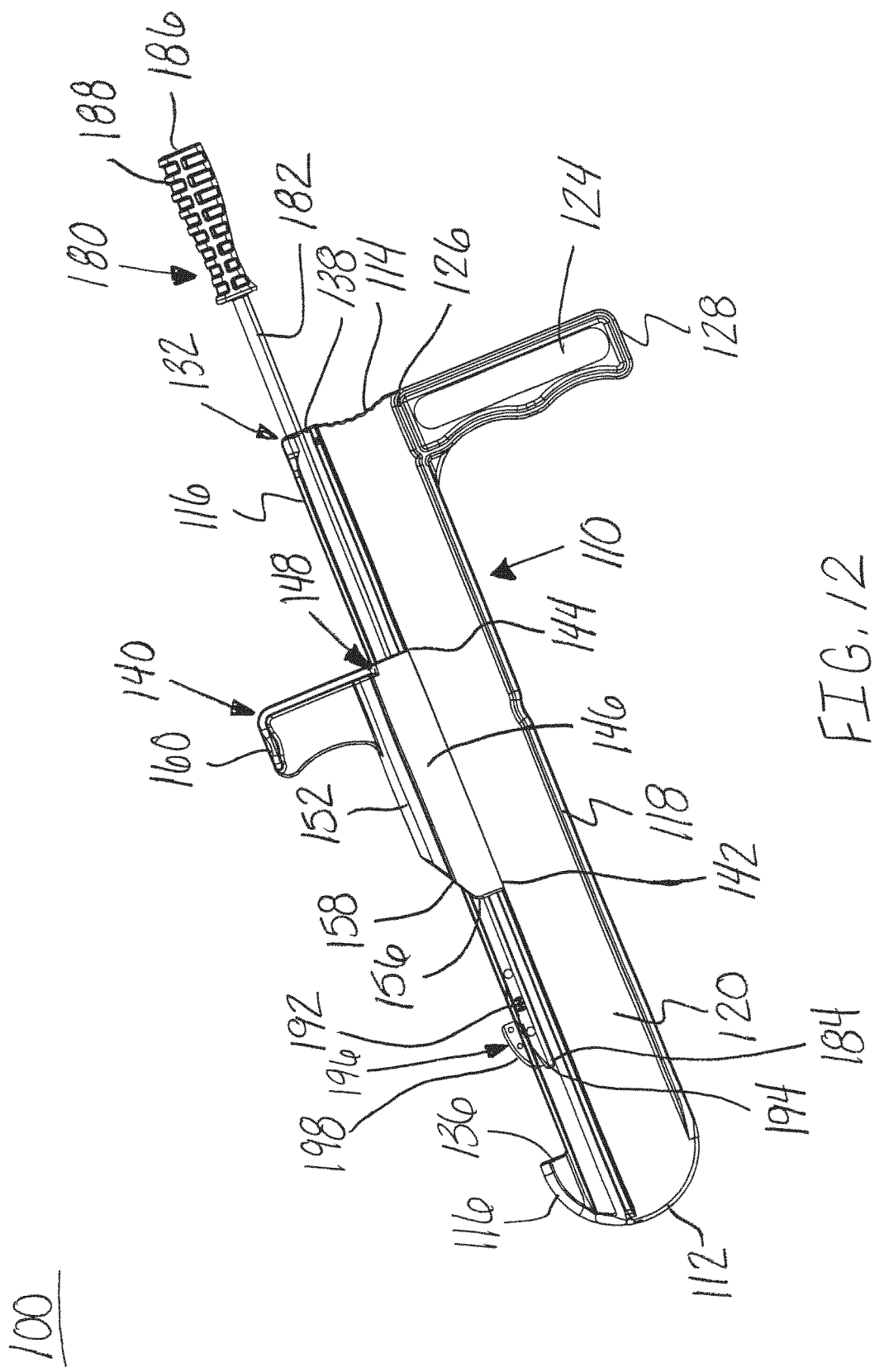
FIG. 12 is a side perspective view of the release instrument of FIG. 1 in a second position with a transparent distractor, in accordance with an aspect of the present invention.
Figure 13:
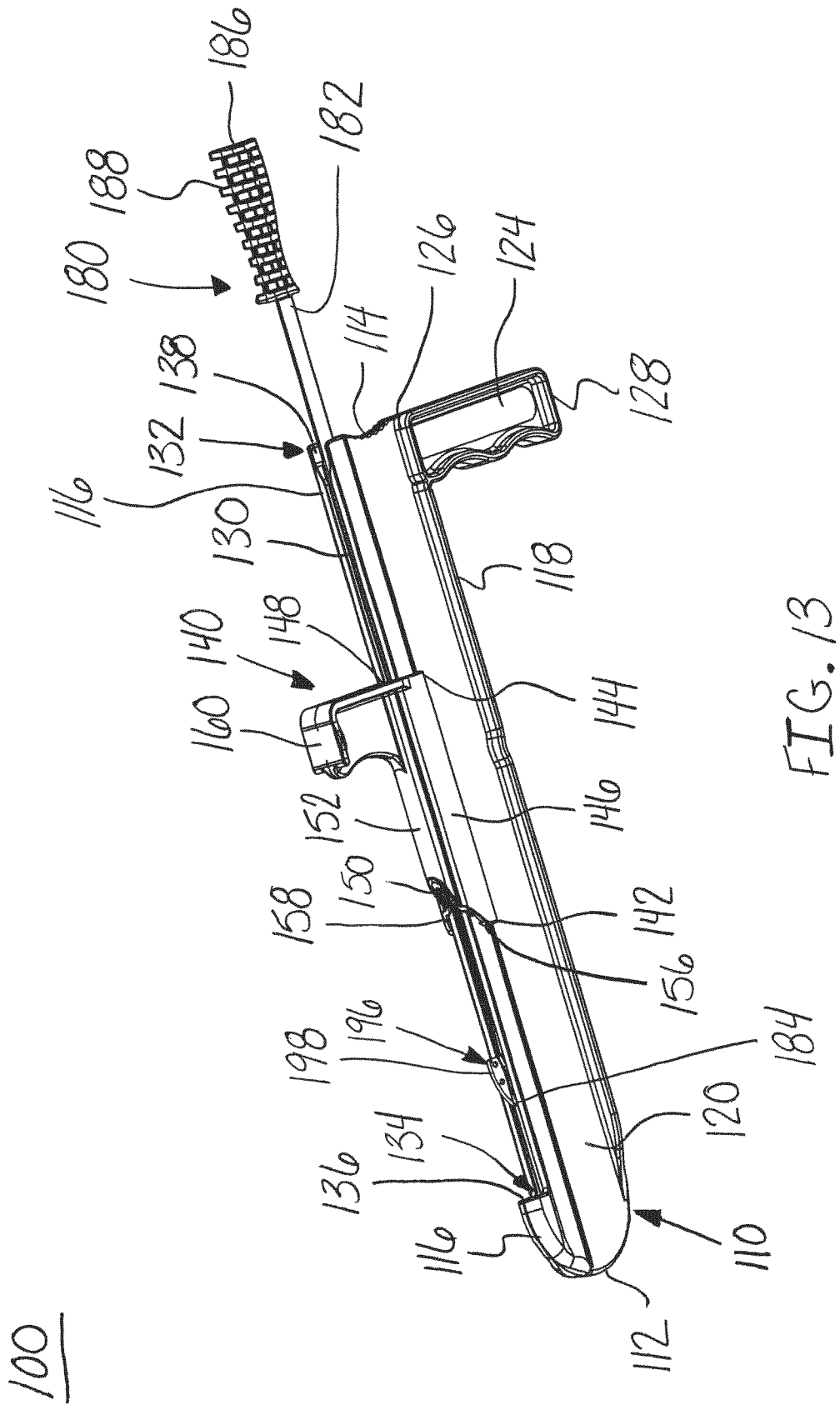
FIG. 13 is a top perspective view of the release instrument of FIG. 12, in accordance with an aspect of the present invention.
Figure 14:
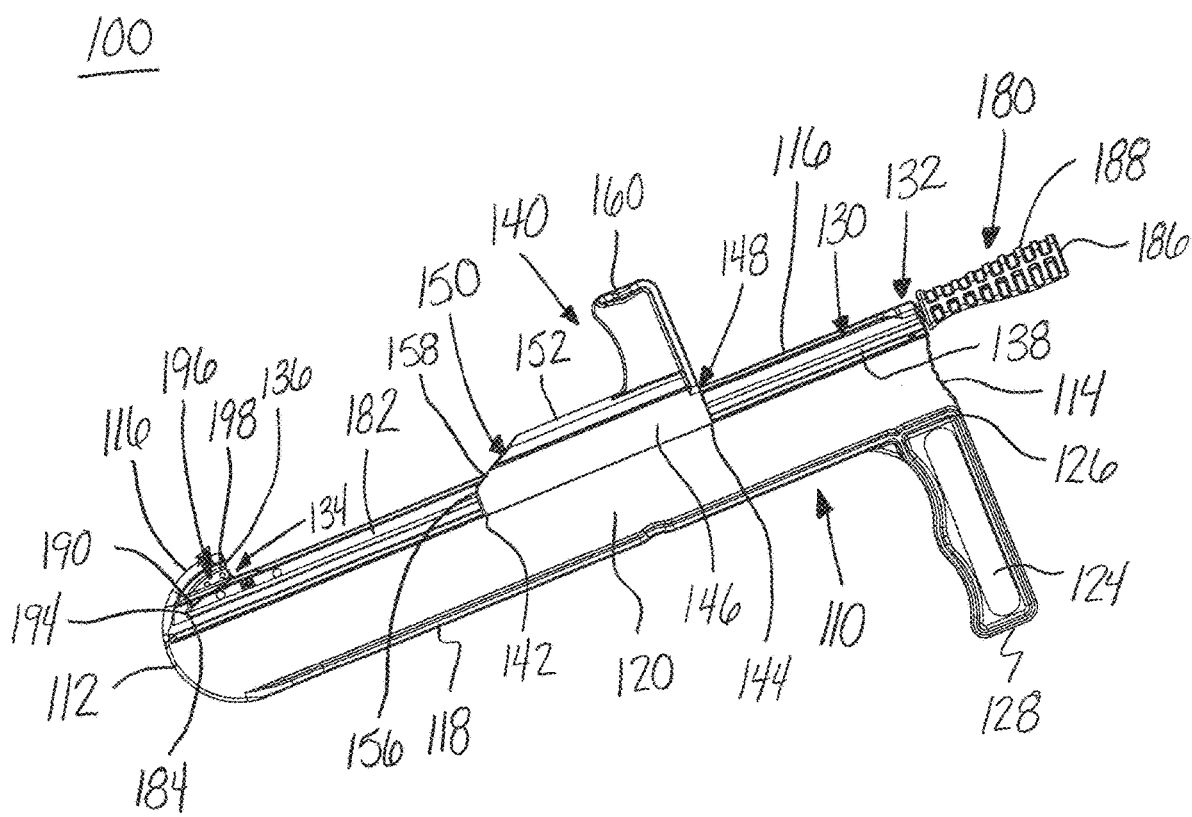
FIG. 14 is a side perspective view of the release instrument of FIG. 1 in a third position with a transparent distractor, in accordance with an aspect of the present invention.
Figure 15:
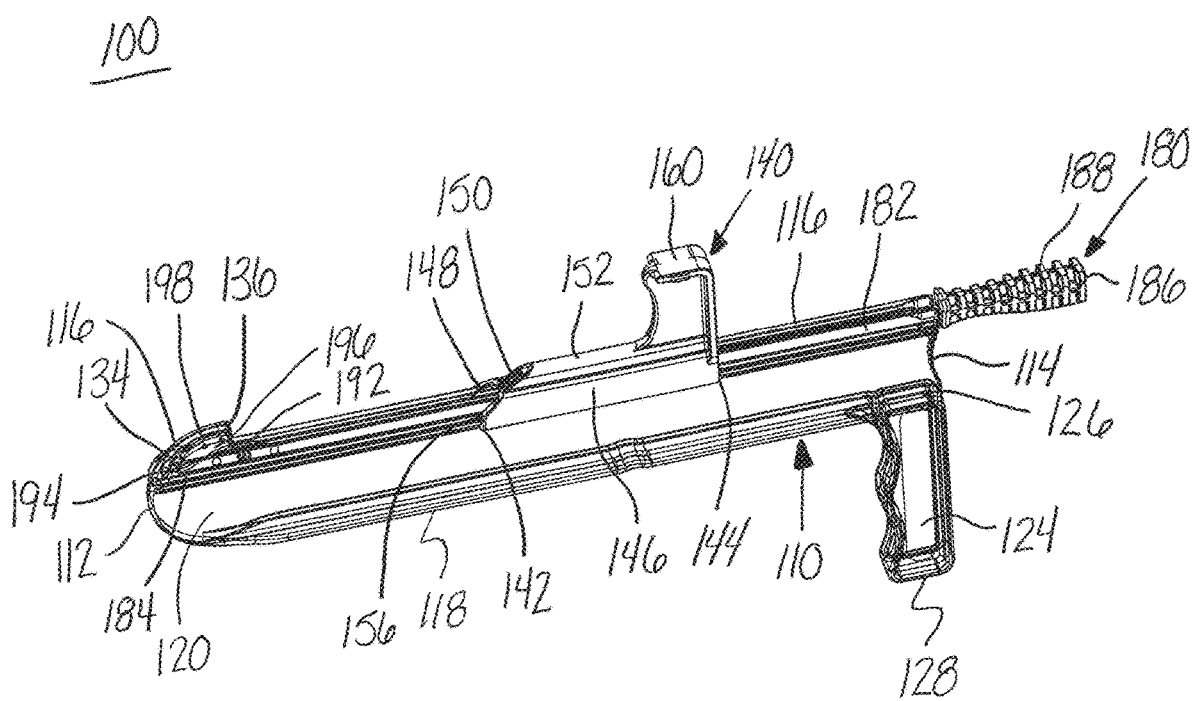
FIG. 15 is a top perspective view of the release instrument of FIG. 14 with a transparent distractor, in accordance with an aspect of the present invention.

The blade member 196 advances through the guide channel 130 of the guide member 110, as shown in FIGS. 11-15. As shown in FIG. 11, the blade member 196 of the blade assembly 180 passes through the protector 140 and into position to cut the selected tissue or fascia. The leading edge of the cutting surface 198 of the blade member 196 may be positioned at or below the top surface of the guide channel 130. Next, as shown in FIGS. 12 and 13, the blade member 196 is advanced through the guide channel 130 along the guide member 110 to cut the tissue or fascia adjacent to the top surface 116 of the guide member 110. Finally, as shown in FIGS. 14 and 15, the blade member 196 is advanced into the cavity 134 completing the cut of the tissue or fascia.

Although the cutting method is described and shown in FIGS. 11-15 with the blade member 196 translating in a distal to proximal direction along the longitudinal axis of the guide member 110, it is also contemplated that the blade member 196 may translate in a proximal to distal direction along the longitudinal axis of the guide member 110. Therefore, the tissue may be cut in either a medial to lateral direction or a lateral to medial direction. For example, the blade member 196 may be positioned within cavity 134 of the guide member 110 during insertion of the guide member 110 into the patient's leg. Once the guide member 110 is rotated and positioned with the guide channel 140 contacting the tissue or fascia to be cut, the handle 188 of the blade assembly 180 may be pulled back to contact the trailing edge of the blade member 196 with the tissue or fascia. The handle 188 may continue to be pulled through the tissue or fascia until the blade member 196 reaches the protector 140 or the second end 114 of the guide member 110.

Figure 18:
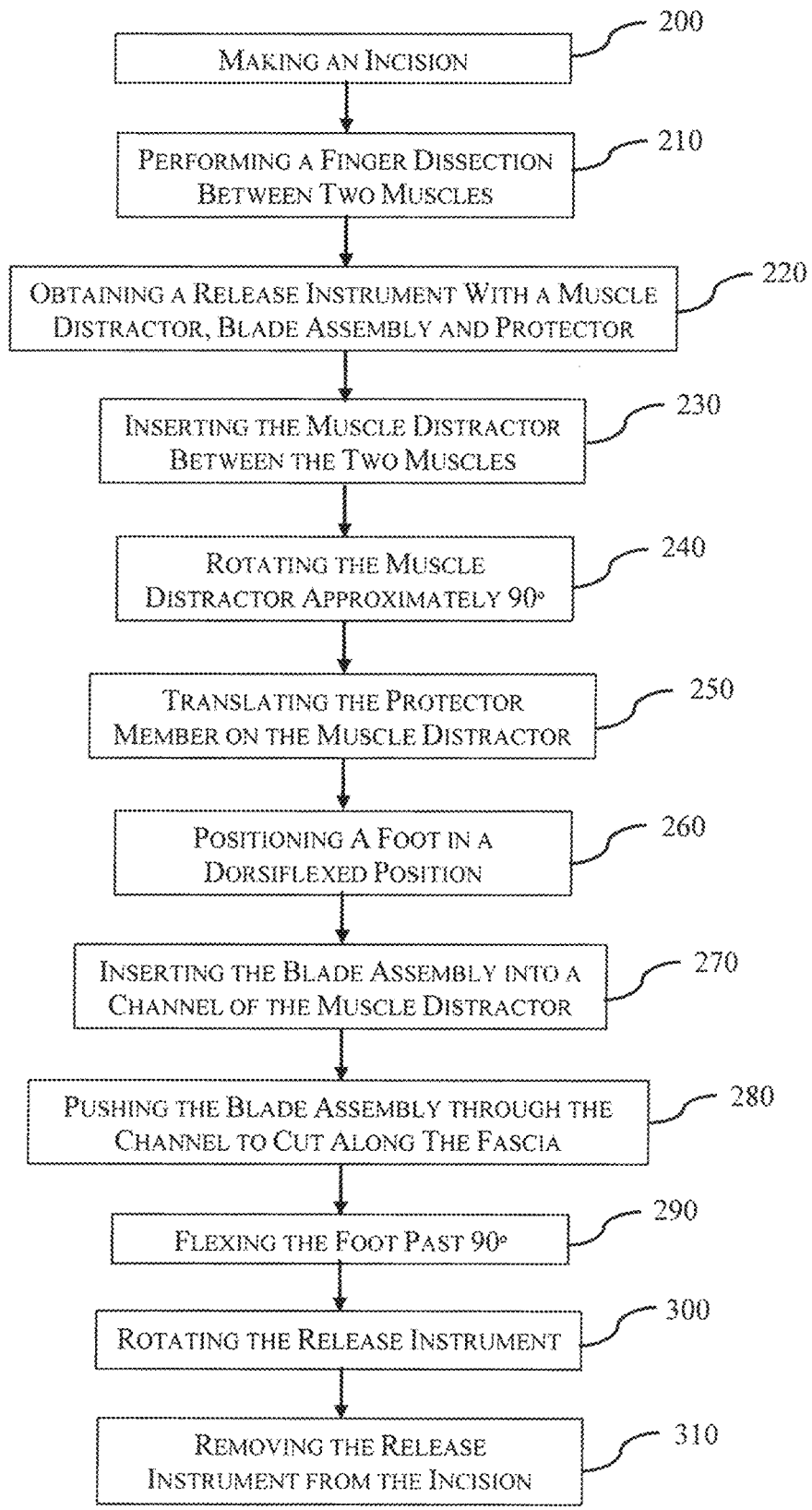
FIG. 18 depicts a method of using the release instrument of FIG. 1, in accordance with an aspect of the present invention.

A method of using the release instrument 100 to cut soft tissue is shown in FIGS. 16-18. The method may include making an incision 200. Next, the method may include performing a finger dissection between at least two muscles or tissue structures 210. Then, a release instrument may be obtained including a muscle distractor, blade assembly, and protector 220, as shown in FIG. 16. After the release instrument is obtained, the distractor may be inserted between the at least two muscles or tissue structures 230. Once the distractor contacts the interior surface of, for example, the opposite lateral skin, the distractor may be rotated, for example, approximately 90° 240, as shown in FIG. 17. Next, a protector member of the release instrument may be coupled to the distractor and translated along a top surface of the distractor 250. The foot may be placed in a dorsiflexed position 260 and a blade assembly inserted into a channel positioned on a top aspect of the distractor 270. Then, the blade assembly may be pushed through the channel from a first end to a second end of the distractor to cut the fascia 280. Next, the foot is flexed past 90° 290 and the release instrument may be rotated again to neutral 300. Finally, the release instrument may be removed from the incision 310 and the patient's incision may be closed.

With continued reference to FIGS. 16-18, an embodiment of the method of using the release instrument 100 to cut soft tissue includes positioning the leg slightly bent and externally rotated. Next, the method includes making an incision 412, for example, a 2.5 mm to 3 mm medial longitudinal incision in the distal third of the calf 400. The soft tissue to be released may be, for example, the tissue that surrounds the gastrocnemius, which when contracted restricts the range of motion of the foot. Next, the method may include performing a finger dissection between at least two muscles or tissue structures 406, 408, 410, for example, between the bellies of the gastrocnemius muscle 408, 410 and the soleus muscle 406. Then, a release instrument 100 may be obtained including a distractor 110, blade assembly 180, and protector 140, as shown in FIG. 16. After the release instrument 100 is obtained, the distractor 110 may be inserted through the incision 412 and between the at least two muscles or tissue structures 406, 408, 410, for example, between the gastrocnemius muscle 408, 410 and the soleus muscle 406 until the distractor 110 contacts and bulges the opposite side skin. The shape of the first end 112 of the distractor 110 allows for integral, blunt dissection of the tissue structures 406, 408, 410 as the distractor 110 is inserted into the patient. Once the distractor 110 contacts the interior surface of, for example, the opposite lateral skin, the distractor 110 may be rotated, for example, approximately 90° to expand the wound, create tension in the fascia, and allow visualization of the fascia of the gastrocnemius muscle 408, 410, as shown in FIG. 17. When the distractor 110 is rotated the tissues are tensioned where the blade member 196 will pass as the blade member 196 is moved with respect to the distractor 110. The tissue is tensioned along the entire portion that will be cut. The distractor 110 is rotated to position the guide channel 130 and contact the tissue or fascia to be cut. When the distractor 110 is rotated, the hook portion 136 engages, for example, the lateral muscle belly of the gastrocnemius 408, as shown in FIG. 17, to stabilize or anchor the distractor 110 and apply tension to the tissues to be cut. Next, a protector member 140 of the release instrument 100 may be coupled to the distractor 110 and translated along a top surface or aspect 116 of the distractor 110. The foot may be placed in a dorsiflexed position and a blade assembly 180 is inserted into a channel 130, 138 positioned on the top surface 116 of the distractor 110. Once the blade assembly 180 is positioned within the channel 130, 138 of the distractor 110, the blade assembly 180 may be pushed through the channel 130, 138 from a second end 114 to a first end 112 of the distractor 110. As the blade assembly 180 is pushed through the channel 130, 138, a cut is made along the fascia at a predetermined depth. Next, as the cut is finished, the foot is flexed past 90°. The blade assembly 180 cuts the fascia, for example, perpendicular to the direction of the muscle tension, allowing the entire muscle complex to lengthen, which returns the patient's joint to full mobility. After the cut is made, the release instrument 100 may be rotated to return the distractor 110 to the insertion position, for example, a position parallel to the muscle bellies 406, 408, 410. Finally, the release instrument 100 may be removed from the incision 412 and the patient's incision 412 may be closed.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method of device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

The invention claimed is:

1. A tissue release instrument, comprising:
    a distractor, comprising:
        a guide channel positioned along an edge of the distractor; and
    a blade assembly;
    the blade assembly engaging the guide channel and configured to slide within the guide channel of the distractor;
    a top and a protector, the protector engaging said top and covering said guide channel, said protector movable along a longitudinal dimension of said top;
    the distractor comprising:
        a first rounded end with a flat portion having a height;
        a handle positioned at a second end;
        a bottom surface opposite a top surface;

a first side; and
a second side opposite the first side;
a hook portion;
the guide channel extending along the top surface from the second end to a position near the first rounded end;
the hook portion positioned near the first rounded end and forming a protrusion extending perpendicular to a longitudinal axis of the distractor; and
the hook portion extending above the guide channel.

2. The instrument of claim 1, wherein the distractor further comprises:
a blade insertion end positioned at the second end, the blade insertion end comprising:
a cavity extending from the second end of the distractor to a position proximate to the hook portion; and
an opening into the guide channel;
wherein the guide channel extends from the top surface of the distractor into the cavity and the blade assembly slidingly engages the cavity and guide channel.

3. The instrument of claim 2, wherein the blade assembly comprises:
a rod;
a cutting blade on a first end of the rod; and
a handle on a second end of the rod opposite the first end.

4. The instrument of claim 3, wherein the rod slidingly engages the cavity to move between the second end and the first rounded end of the distractor.

5. The instrument of claim 4, wherein the guide channel receives the cutting blade as the rod of the blade assembly moves along the distractor.

6. The instrument of claim 3, wherein the cutting blade extends out from the guide channel of the distractor beyond the top surface of the distractor.

7. The instrument of claim 1, wherein the protector comprises:
an engagement member extending from a first end to a second end of the protector; and
a handle extending away from the second end of the engagement member.

8. The instrument of claim 7, wherein the engagement member comprises:
a through hole extending from the first end to the second end;
a passageway extending from the first end to the second end, the passageway positioned proximal to and extending into the through hole; and
an engagement channel extending from the first end to the second end, the engagement channel positioned distal to and extending from an exterior surface into the through hole.

9. The instrument of claim 8, wherein the through hole slidingly engages a top portion of the distractor, the passageway is aligned with the guide channel of the distractor, a first side of the engagement channel is positioned adjacent to the first side of the distractor, and a second side of the engagement channel is positioned adjacent to the second side of the distractor.

10. The instrument of claim 8, wherein a cutting blade of the blade assembly is slidingly received within the passageway of the protector.

11. The instrument of claim 7, wherein the engagement member further comprises:
a leading edge positioned at the first end of the protector; and
a tapered portion extending from the leading edge to a top surface of the protector.

12. A tissue release instrument, comprising:
a distractor, comprising:
a guide channel positioned along an edge of the distractor; and
a blade assembly;
the blade assembly engaging the guide channel and configured to slide within the guide channel of the distractor;
a top and a protector, the protector engaging said top and covering said guide channel, said protector movable along a longitudinal dimension of said top;
the protector comprising:
an engagement member extending from a first end to a second end of the protector;
a handle extending away from the second end of the engagement member;
the engagement member comprising:
a through hole extending from the first end to the second end;
a passageway extending from the first end to the second end, the passageway positioned proximal to and extending into the through hole; and
an engagement channel extending from the first end to the second end, the engagement channel positioned distal to and extending from an exterior surface into the through hole.

* * * * *